(12) United States Patent
Ikeda

(10) Patent No.: US 8,591,525 B2
(45) Date of Patent: Nov. 26, 2013

(54) HEMORRHOID LIGATION APPARATUS, LIGATION KIT CONTAINING THE APPARATUS AND METHOD FOR LIGATING HEMORRHOID

(75) Inventor: Masao Ikeda, Akita (JP)

(73) Assignee: Sumitomo Bakelite Company, Ltd., Tokyo (JP)

( * ) Notice: Subject to any disclaimer, the term of this patent is extended or adjusted under 35 U.S.C. 154(b) by 1687 days.

(21) Appl. No.: 12/071,057

(22) Filed: Feb. 14, 2008

(65) Prior Publication Data

US 2009/0198255 A1 Aug. 6, 2009

(30) Foreign Application Priority Data

Feb. 6, 2008 (JP) .................................. 2008-026510

(51) Int. Cl.
*A61B 17/12* (2006.01)
(52) U.S. Cl.
USPC ........... 606/140; 606/141; 606/206; 128/831; 29/235
(58) Field of Classification Search
USPC .................................................. 606/139–141
See application file for complete search history.

(56) References Cited

U.S. PATENT DOCUMENTS

| 4,217,686 | A | * | 8/1980 | Dragan ........................... 29/413 |
| 5,741,273 | A | | 4/1998 | O'Regan |
| 6,099,535 | A | * | 8/2000 | Lamport et al. .............. 606/140 |
| 6,436,108 | B1 | * | 8/2002 | Mears ........................... 606/140 |
| 2003/0130559 | A1 | | 7/2003 | Morin et al. |

FOREIGN PATENT DOCUMENTS

| JP | 2000-254131 | 9/2000 |
| JP | 2004-167257 | 6/2004 |

* cited by examiner

*Primary Examiner* — Vy Q Bui
(74) *Attorney, Agent, or Firm* — Smith, Gambrell & Russell, LLP

(57) ABSTRACT

The hemorrhoid ligation apparatus (10) includes a main cylinder (12) to which an O-ring (50) for ligating the hemorrhoid is to be attached on an outer circumferential surface of a front end portion, a sub cylinder (14) air-tightly and slidably provided inside the main cylinder (12), so as to suck the hemorrhoid into the front end portion of the main cylinder (12) upon being drawn toward a rear end portion of the main cylinder (12), an operating fluid loaded inside the sub cylinder (14), and a plunger (16) air-tightly and slidably provided inside the sub cylinder (14), so as to pressurize the operating fluid upon being squeezed toward a front end portion of the sub cylinder (14), to thereby squeeze the O-ring (50) toward the front end portion of the main cylinder (12) with the pressurized operating fluid, thus detaching the O-ring (50) from the main cylinder (12).

9 Claims, 8 Drawing Sheets

HEMORRHOID LIGATION APPARATUS, LIGATION KIT CONTAINING THE APPARATUS AND METHOD FOR LIGATING HEMORRHOID

This application is based on Japanese patent application No. 2008-026,510, the content of which is incorporated hereinto by reference.

TECHNICAL FIELD

The present invention relates to a hemorrhoid ligation apparatus to be used with an O-ring for ligating a hemorrhoid, a ligation kit that includes the ligation apparatus, and to a method of ligating the hemorrhoid.

BACKGROUND ART

Regarding such type of techniques, JP-A No. 2000-254131 cited here below describes a ligation apparatus that sucks the hemorrhoid with a negative pressure through a forceps hole of an endoscope inserted into a tubular body, and then detaches, with a fluid injected from a syringe or the like, an O-ring attached in advance to a front end portion of the tubular body, to thereby ligate the hemorrhoid.

Also, JP-A No. 2004-167257 and U.S. Pat. No. 5,741,273 cited below describe a ligation apparatus that sucks the hemorrhoid utilizing a housing with an O-ring attached to a front end portion thereof and a plunger, and then detaches the O-ring by pushing a thumb pusher provided outside the housing toward the front end portion, to thereby ligate the hemorrhoid.

Those ligation apparatuses are employed in combination with a funnel-shaped anoscope. Accordingly, the operator such as a doctor uses a hand to insert a small-diameter tip portion of the anoscope into the anus of the patient, and the other hand to operate the ligation apparatus.

[Patented document 1] JP-A No. 2000-254131
[Patented document 2] JP-A No. 2004-167257
[Patented document 3] U.S. Pat. No. 5,741,273

DISCLOSURE OF THE INVENTION

Problem to be Solved by the Invention

In the ligation apparatus according to the patented document 1, however, the endoscope that generates the negative pressure for sucking the hemorrhoid and the syringe for detaching the O-ring are independently provided, and hence it is difficult for the operator to handle the ligation apparatus with either hand only, when the operator also has to handle the anoscope in combination.

In contrast, the ligation apparatus according to the patented documents 2 and 3 includes the housing and the plunger integrated inside the thumb pusher, and therefore allows the operator to draw the plunger so as to suck the hemorrhoid (hereinafter, the suction of the hemorrhoid may be referred to as "first operation"), and to push the thumb pusher so as to detach the O-ring (hereinafter, the detaching the O-ring may be referred to as "second operation"), both with a single hand.

However, in the case of operating the ligation apparatus according to the patented documents 2 and 3, if the operator accidentally touches the thumb pusher during the first operation of drawing the plunger, the O-ring is detached from the housing before the hemorrhoid is sucked, which disables the operator from ligating the hemorrhoid. Thus, such ligation apparatus strictly limits the operation mode such as the retaining position thereof, and hence readily provokes improper operation, which leads to the drawback that high expertise in operation is required.

The present invention has been achieved in view of the foregoing problem, and provides a hemorrhoid ligation apparatus that allows the operator to handle with a single hand to ligate the hemorrhoid under minimized risk of committing improper operation, a ligation kit including such ligation apparatus, and a method of ligating the hemorrhoid.

Means for Solving Problem

According to the present invention, there is provided a hemorrhoid ligation apparatus, comprising:
a main cylinder to which an O-ring for ligating the hemorrhoid is to be attached, on an outer circumferential surface of a front end portion;
a sub cylinder air-tightly and slidably provided inside the main cylinder, so as to suck the hemorrhoid into inside the front end portion of the main cylinder upon being drawn toward a rear end portion of the main cylinder;
an operating fluid loaded inside the sub cylinder; and
a plunger air-tightly and slidably provided inside the sub cylinder, so as to pressurize the operating fluid upon being squeezed toward a front end portion of the sub cylinder, to thereby squeeze the O-ring toward the front end portion of the main cylinder with the operating fluid being pressurized, thus detaching the O-ring from the main cylinder.

The hemorrhoid ligation apparatus according to the present invention may further comprise, as a more specific structure, a piping having an end communicating with the sub cylinder so as to allow the operating fluid to flow through the piping;
a sliding member slidably attached to an outer circumferential surface of the front end portion of the main cylinder, so as to seal the other end of the piping and to squeeze the O-ring toward the front end portion of the main cylinder according to a pressing force applied by the operating fluid being pressurized;
a front end stopper that delimits a forward movable range of the sliding member; and
a rear end stopper that delimits a backward movable range of the sliding member.

As a more specific structure of the hemorrhoid ligation apparatus according to the present invention, a front end of the sliding member may become flush with or recessed from the front end of the main cylinder, upon reaching a dead point of the forward movable range.

The hemorrhoid ligation apparatus according to the present invention may further comprise, as a more specific structure, a fixing member that fixes a relative position of the sub cylinder drawn backward and the main cylinder.

As a more specific structure of the hemorrhoid ligation apparatus according to the present invention, the main cylinder may be constituted of a transparent material.

As a more specific structure of the hemorrhoid ligation apparatus according to the present invention, the front end portion of the main cylinder constitutes an extended portion of the main cylinder, along a sliding direction of the sub cylinder, and
the sub cylinder and the plunger may both be constituted of a transparent material.

Alternatively, the front end portion of the main cylinder may include an extension in a direction that intersects with the sliding direction of the sub cylinder.

According to the present invention, there is provided a ligation kit comprising the foregoing hemorrhoid ligation apparatus, the O-ring attached to an outer circumferential surface of the front end portion of the main cylinder, an O-ring attaching device including (a) a tubular body having a larger inner diameter than an outer diameter of the front end portion of the main cylinder, (b) a substrate including at least one hole through which the tubular body is to be slidably inserted, and (c) a tapered-shape expanding device having a tip portion smaller in diameter than a base portion thereof, to be fitted on an upper end portion of the tubular body exposed through the hole, via the base portion.

According to the present invention, there is provided a method of ligating a hemorrhoid with an O-ring attached to an outer circumferential surface of a front end portion of a main cylinder, comprising:

a first process including drawing a sub cylinder air-tightly and slidably provided inside the main cylinder and a plunger air-tightly and slidably provided inside the sub cylinder together toward a rear end portion of the main cylinder, to thereby suck the hemorrhoid into inside the front end portion of the main cylinder; and a second process including squeezing the plunger toward a front end portion of the sub cylinder to thereby pressurize an operating fluid loaded inside the sub cylinder, so as to cause the operating fluid being pressurized to squeeze the O-ring toward the front end of the main cylinder thus detaching the O-ring from the main cylinder, and ligating the hemorrhoid with the O-ring thus detached.

The constituents of the present invention do not have to be individually independent, but a plurality of constituents may constitute a single member; a plurality of elements may constitute a single constituent; a constituent may form a part of another constituent; a part of a constituent and a part of another constituent may overlap; and so forth.

The term of "air-tight" according to the present invention does not necessarily mean that a fluid is strictly inhibited from leaking or intruding, but such extent of air-tightness that allows achieving the object of the present invention by operating various constituents.

Also, the operating fluid according to the present invention may be any material having fluidity, including liquid, gas, powder, gel, or any combination thereof.

Effect of the Invention

In the hemorrhoid ligation apparatus according to the present invention, the main cylinder includes therein the sub cylinder, and the sub cylinder includes therein the plunger. Accordingly, when performing the first operation of sucking the hemorrhoid into the main cylinder, the operator can draw the sub cylinder and the plunger from the main cylinder, with either hand only. Also, when performing the second operation of detaching the O-ring from the main cylinder to thereby ligate the hemorrhoid, the operator can squeeze the plunger into the sub cylinder, only with either hand. Thus, the hemorrhoid ligation apparatus according to the present invention allows the operator to operate with only one hand, and hence allows the operator to ligate the hemorrhoid retaining an anoscope with the other hand.

Also, in the hemorrhoid ligation apparatus according to the present invention, the main cylinder and the plunger move relatively away from each other in the first operation, the main cylinder and the plunger move relatively closer to each other, in the second operation. In other words, the moving direction of the plunger, which serves to detach the O-ring, turns opposite upon entering the second operation from the first operation, with respect to the main cylinder with the O-ring attached thereto. The hemorrhoid ligation apparatus according to the present invention prevents, therefore, the operator from committing such improper operation as accidentally detaching the O-ring during the first operation.

Further, the ligation kit according to the present invention allows the operator to easily attach the O-ring to the hemorrhoid ligation apparatus which offers the foregoing advantages.

BRIEF DESCRIPTION OF THE DRAWINGS

The above and other objects, advantages and features of the present invention will be more apparent from the following description taken in conjunction with the accompanying drawings, in which.

BEST MODE FOR CARRYING OUT THE INVENTION

The invention will be now described herein with reference to illustrative embodiments. Those skilled in the art will recognize that many alternative embodiments can be accomplished using the teachings of the present invention and that the invention is not limited to the embodiments illustrated for explanatory purposes.

Hereunder, embodiments of the present invention will be described, referring to the accompanying drawings. In all the drawings, same constituents will be given the same numeral, and the description thereof will not be repeated.

First Embodiment

Figure 1:
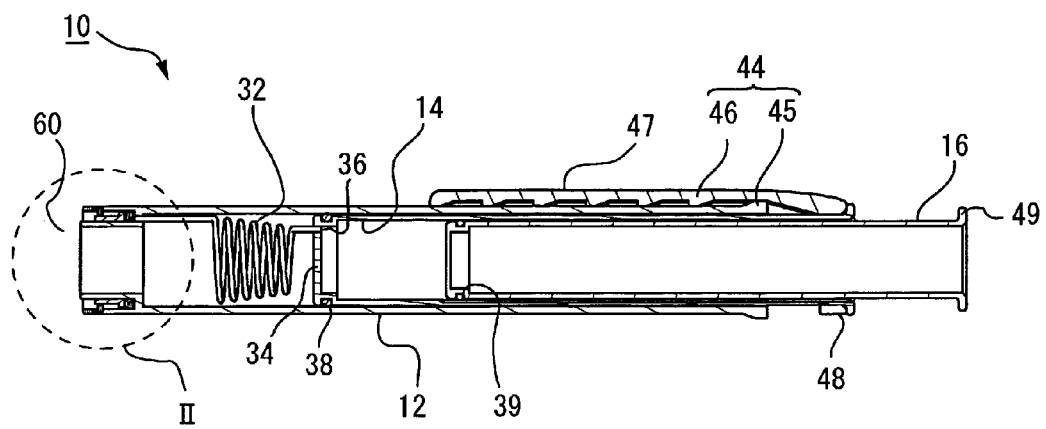
FIG. 1 is a vertical cross-sectional view showing a hemorrhoid ligation apparatus according to a first embodiment of the present invention.

FIG. 1 is a vertical cross-sectional view showing a hemorrhoid ligation apparatus 10 according to a first embodiment of the present invention, taken along a sliding direction of a sub cylinder 14 and a plunger 16.

Figure 2:
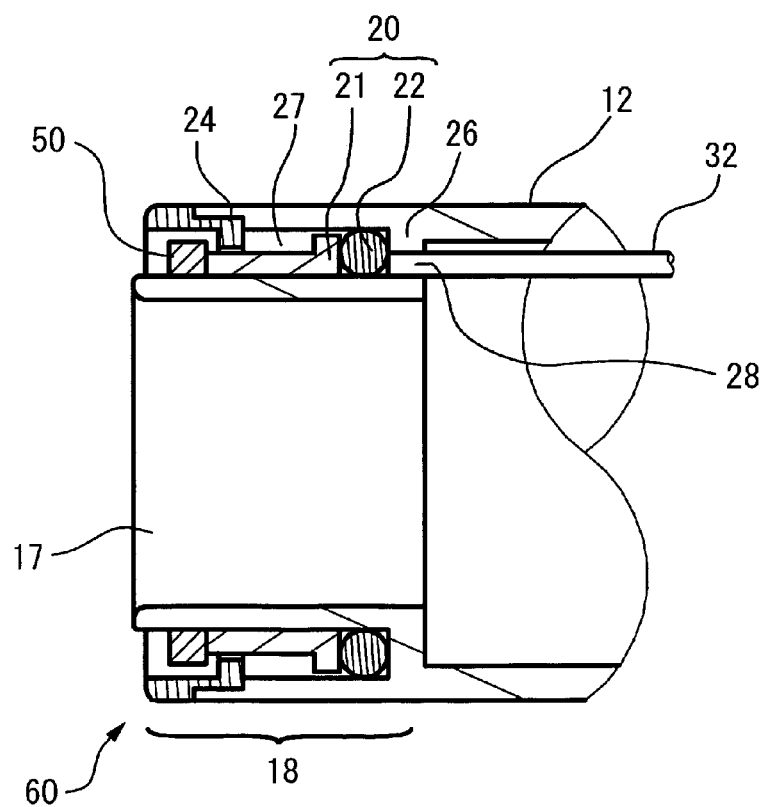
FIG. 2 is an enlarged drawing of a front end portion of the hemorrhoid ligation apparatus according to the embodiment.

FIG. 2 is an enlarged drawing of a portion enclosed by a circle II in FIG. 1, showing a front end portion 60 of the hemorrhoid ligation apparatus 10 according to this embodiment.

Figure 3A:
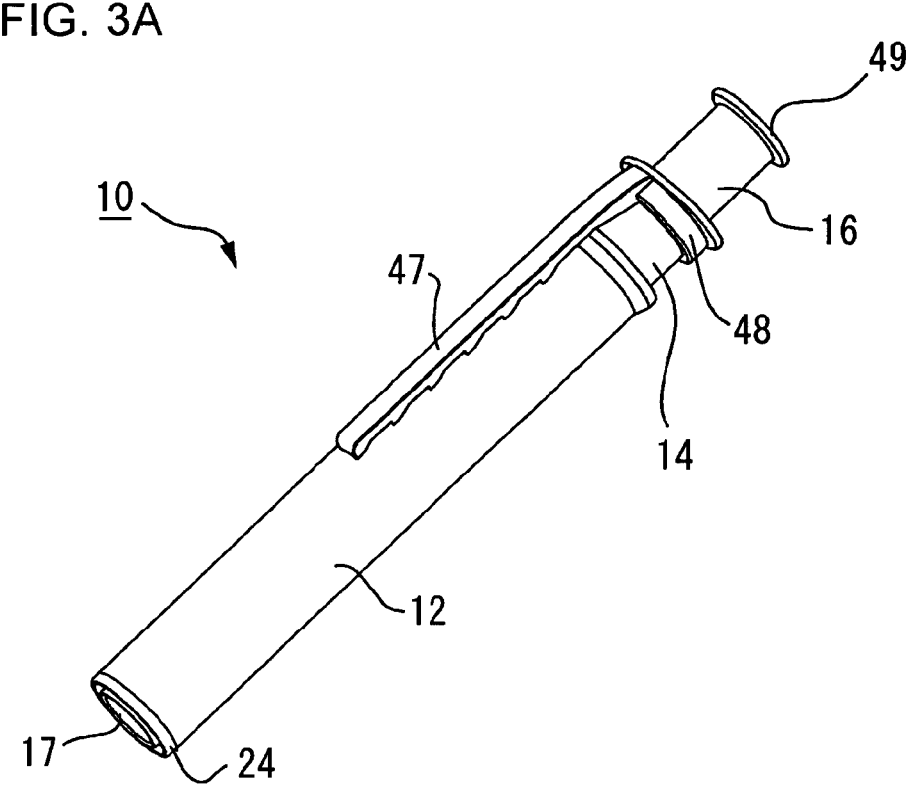
FIG. 3A is a perspective view showing the hemorrhoid ligation apparatus according to the embodiment, and FIG. 3B a perspective view showing an internal structure of the hemorrhoid ligation apparatus.
Figure 3B:
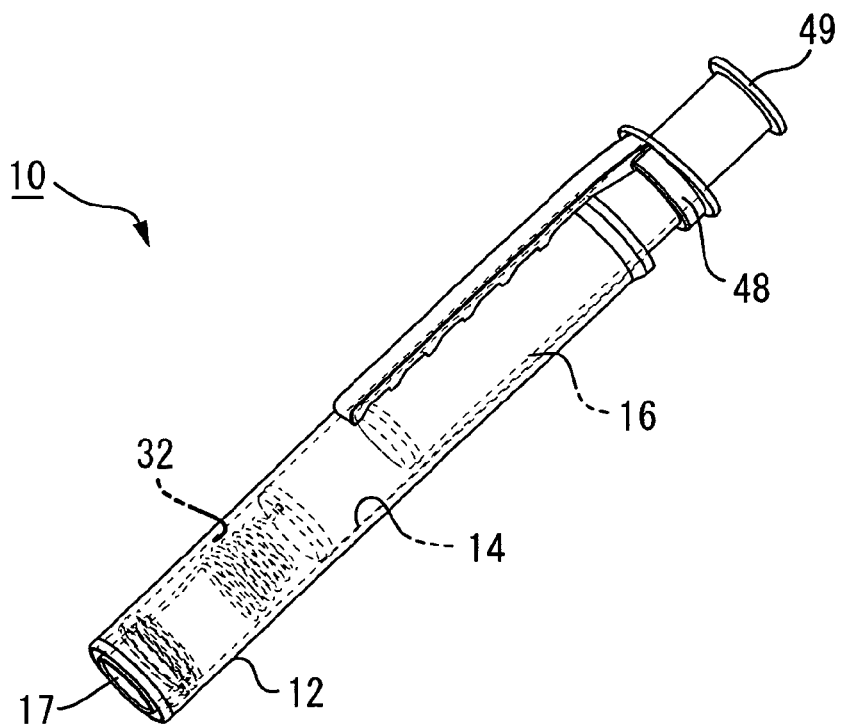

FIG. 3A is a perspective view showing the hemorrhoid ligation apparatus 10 according to this embodiment, and FIG. 3B a perspective view showing an internal structure thereof.

Figure 4A:
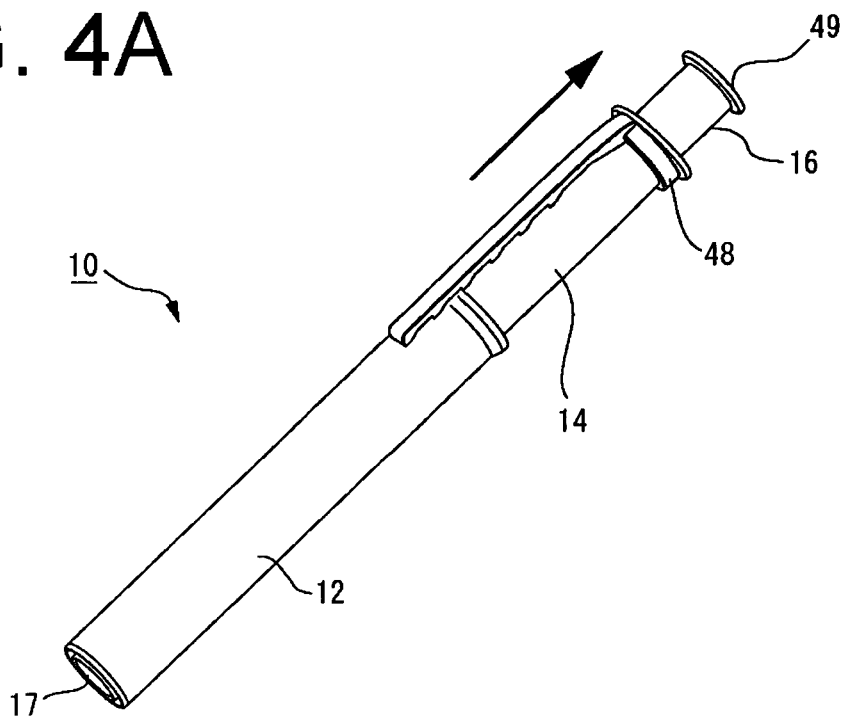
FIG. 4A is a perspective view showing the hemorrhoid ligation apparatus after the first operation, and FIG. 4B a perspective view showing the hemorrhoid ligation apparatus after the second operation.
Figure 4B:
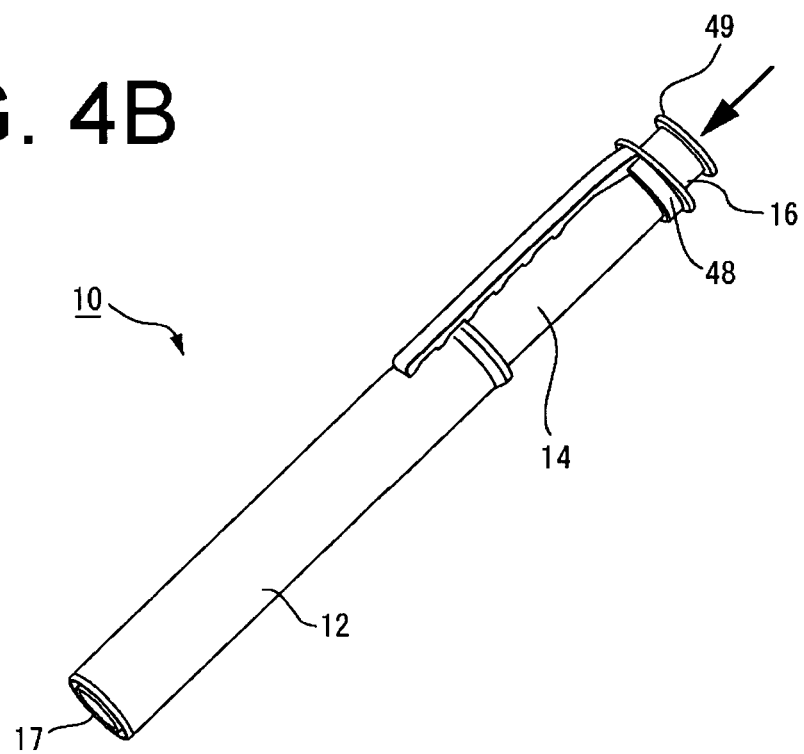

FIG. 4A is a perspective view showing the hemorrhoid ligation apparatus 10 after the first operation, and FIG. 4B a perspective view showing the hemorrhoid ligation apparatus 10 after the second operation.

Figure 5A:
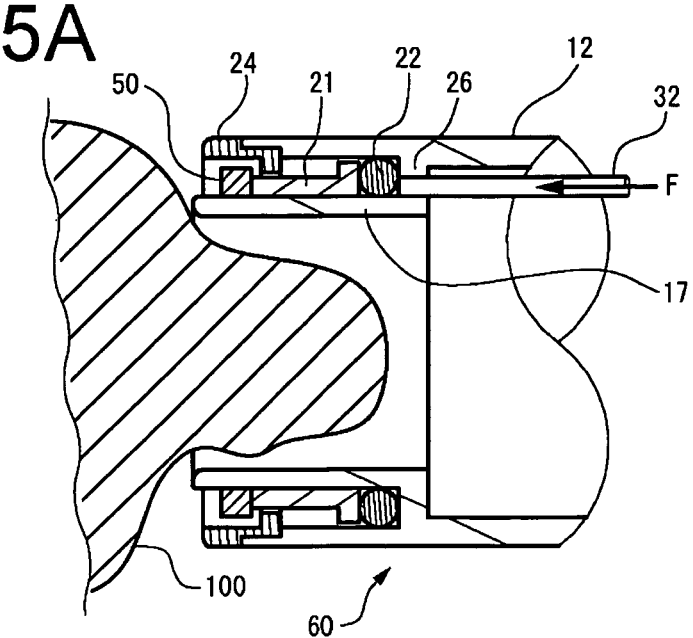
FIG. 5A is a vertical cross-sectional view showing the front end portion of the hemorrhoid ligation apparatus and a hemorrhoid being sucked thereinto, at the start of the second operation, and FIG. 5B a vertical cross-sectional view showing the hemorrhoid ligation apparatus and the hemorrhoid, at the end of the second operation.
Figure 5B:
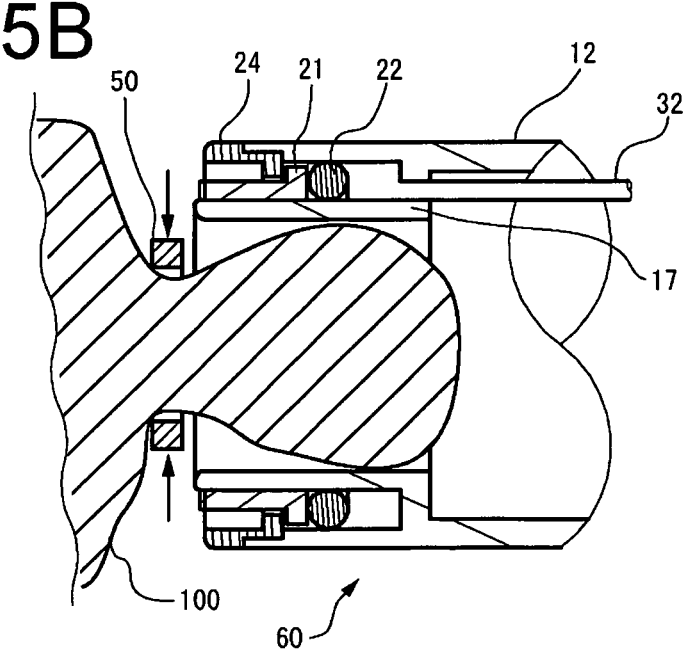
Figure 6:
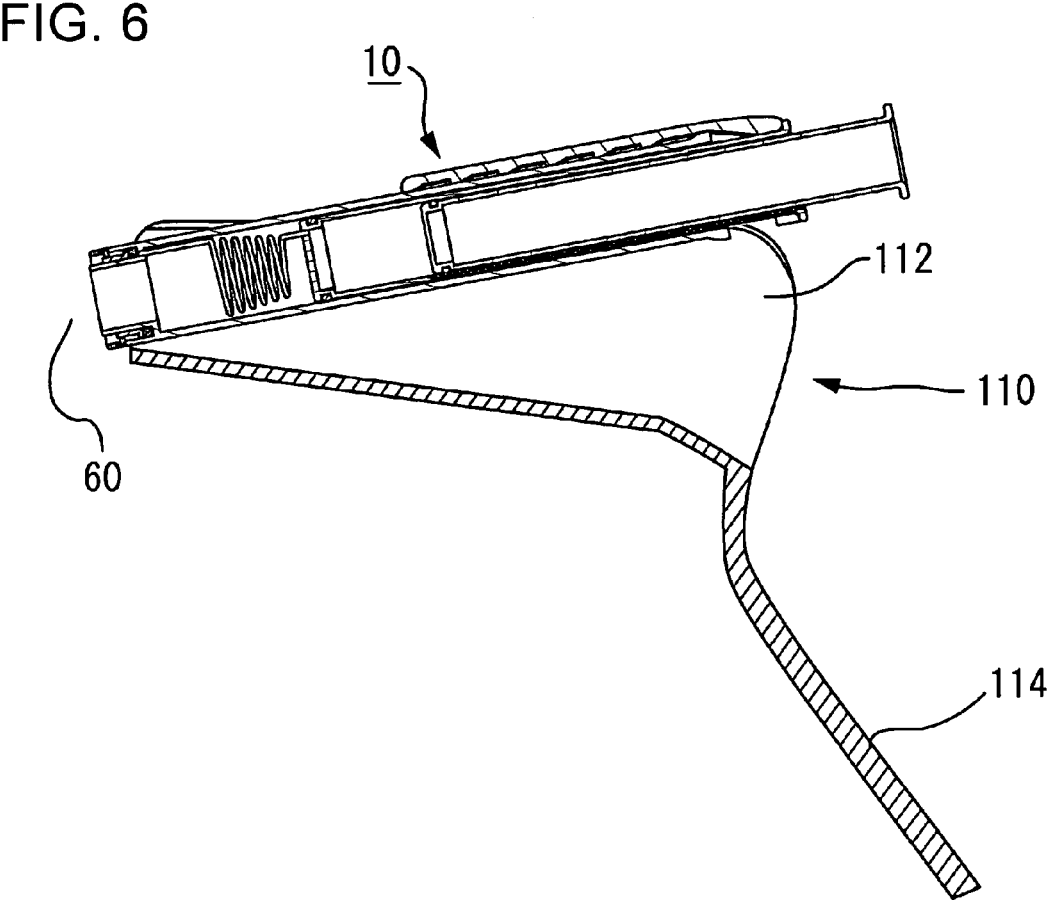
FIG. 6 shows the hemorrhoid ligation apparatus according to the first embodiment mounted on an anoscope, for actual use.

FIG. 5A is a vertical cross-sectional view showing the front end portion 60 of the hemorrhoid ligation apparatus 10 and a hemorrhoid 100 being sucked thereinto, at the start of the second operation, and FIG. 5B a vertical cross-sectional view showing the hemorrhoid ligation apparatus 10 and the hemorrhoid 100, at the end of the second operation;

FIG. 6 shows the hemorrhoid ligation apparatus 10 mounted on an anoscope 110, for actual use;

Firstly, the outline of the hemorrhoid ligation apparatus 10 according to this embodiment will be described.

The hemorrhoid ligation apparatus 10 includes a main cylinder 12, to which an O-ring 50 for ligating a hemorrhoid 100 (Ref. FIGS. 5A and 5B) is to be attached, on an outer circumferential surface of a front end portion.

The hemorrhoid ligation apparatus 10 also includes a sub cylinder 14 air-tightly and slidably provided inside the main cylinder 12, so as to suck the hemorrhoid 100 into inside the front end portion of the main cylinder 12, upon being drawn backward with respect to the main cylinder 12. Inside the sub cylinder 14, an operating fluid F is loaded.

The hemorrhoid ligation apparatus 10 also includes a plunger 16 air-tightly and slidably provided inside the sub cylinder 14, so as to pressurize the operating fluid F upon being squeezed toward a front end portion of the sub cylinder 14, to thereby cause the pressurized operating fluid F to squeeze the O-ring 50 toward the front end of the main cylinder 12, thus detaching the O-ring 50 from the main cylinder 12.

Now, further details of the hemorrhoid ligation apparatus 10 according to this embodiment will be described.

The main cylinder 12 is of a tubular shape, in which the sub cylinder 14 is inserted through a rear end portion. The front end portion 60 of the main cylinder 12 has a double-wall structure including a suction tube 17 around which the O-ring 50 is to be attached, and a cover tube 18 provided on an outer side of the suction tube 17.

The sub cylinder 14 serves as a cylinder for the plunger 16 inserted thereinto, and also as a plunger that slides with respect to the main cylinder 12.

The main cylinder 12 and the sub cylinder 14 are air-tightly sealed by a seal ring 38. Also, the sub cylinder 14 and the plunger 16 are air-tightly sealed by a seal ring 39.

The sub cylinder 14 includes a radially projecting engaging portion 48 formed at a rear end portion (right-hand side in FIGS. 1 and 2), for the operator to engage his/her finger.

Accordingly, in the first operation of sucking the hemorrhoid 100, the operator may hold the main cylinder 12 with his/her fingers (for example, with two fingers of index finger and middle finger, or three fingers of thumb, index finger and middle finger), and engage other fingers of the same hand (for example the thumb and ring finger, or the ring finger alone) with the engaging portion 48, to easily draw the sub cylinder 14 from the main cylinder 12. Thus, a negative pressure is generated inside the suction tube 17, and the hemorrhoid 100 is thereby sucked into a front end portion (left-hand side in FIGS. 1 and 2) of the suction tube 17.

It is to be noted that, in this embodiment, "front" or "forward" means the front end side of the hemorrhoid ligation apparatus 10 where the O-ring 50 is attached, and "rear" or "backward" means the rear end side of the main cylinder 12, where the sub cylinder 14 and the plunger 16 are provided.

The plunger 16 includes, at a rear end portion thereof, a flange portion 49, for the operator to squeeze the plunger 16 forward with respect to the sub cylinder 14, in the second operation of detaching the O-ring 50.

The hemorrhoid ligation apparatus 10 according to this embodiment includes a piping 32, having an end communicating with the sub cylinder 14, so that the operating fluid F flows therethrough.

Accordingly, when the plunger 16 is squeezed forward to thereby increase the internal pressure of the sub cylinder 14, the operating fluid F loaded therein is squeezed out through the piping 32.

The sub cylinder 14 includes a fluid hole 36 formed through a front end face 34 thereof, to which the end of the piping 32 is attached so as to communicate with the sub cylinder 14. The other end (front end) of the piping 32 is attached to a fluid hole 28 provided on the front end portion 60 of the main cylinder 12, as shown in FIG. 2. Here, the piping 32 according to this embodiment is helically wound so as to expand or shrink, and enclosed in the main cylinder 12. Accordingly, when the sub cylinder 14 slides with respect to the main cylinder 12 (suction tube 17), the piping 32 is deformed so as to expand or shrink.

Also, the helical structure of the piping 32 accepts therein a larger amount of the operating fluid F, which provided a larger "play" upon squeezing the plunger 16, before the operating fluid F is squeezed out at the front end.

Hereunder, description will be given on a method of actually squeezing out the O-ring with the pressurized operating fluid F thereby detaching the same, with the hemorrhoid ligation apparatus 10 according to this embodiment.

The main cylinder 12 according to this embodiment includes a sliding member 20 slidably attached to an outer circumferential surface of the front end portion, so as to seal the other end (front end) of the piping 32. The sliding member 20 serves to squeeze out the O-ring 50 toward the front end of the main cylinder 12, because of the pressing force of the pressurized operating fluid F.

The sliding member 20 according to this embodiment is a combination of a seal member 22 slidably attached between the cover tube 18 and the suction tube 17, and a sleeve 21, a rear end face of which is to be pressed forward by the seal member 22. Here, the sleeve 21 and the seal member 22 may be integrally formed.

More specifically, the seal member 22 is constituted of a seal ring made of a soft resin material such as a silicone rubber, and the sleeve 21 is constituted of a tubular body made of a hard resin material such as a plastic.

The sleeve 21 and the seal member 22 can slide back and forth in a clearance 27 formed between the cover tube 18 and the suction tube 17. Although the other end (front end) of the piping 32 communicates with the clearance 27, the operating fluid F inside the piping 32 is locked in a closed space defined by the inner surface of the cover tube 18, the seal member 22 and the outer surface of the suction tube 17.

Now, as indicated by an arrow in FIG. 5A, when the pressurized operating fluid F pushes the seal member 22 forward, the seal member 22 and the sleeve 21 slides forward together, so that the front end face of the sleeve 21 squeezes the O-ring 50.

Also, the hemorrhoid ligation apparatus 10 according to this embodiment includes a front end stopper 24 that delimits the forward movable range of the sliding member 20, and a rear end stopper 26 that delimits the backward movable range of the sliding member 20.

The front end stopper 24 provided on the front end side of the clearance 27 is of a ring shape, and the front end stopper 24 has an inner diameter smaller than the diameter of a largest portion of the sleeve 21. The front end stopper 24 is attached to the cover tube 18 of the main cylinder 12, from the front end thereof. The sleeve 21 squeezed by the operating fluid F is butted to the front end stopper 24, thereby reaching a dead point of the forward movable range (Ref. FIG. 5B).

Meanwhile, the rear end stopper 26 provided on the rear end side of the clearance 27 is formed so as to protrude from the suction tube 17 or the cover tube 18 into the clearance 27. In this embodiment, the rear end stopper 26 inwardly protrudes from an inner surface of the cover tube 18. Upon drawing the plunger 16 from the sub cylinder 14 to thereby reduce the pressure to the operating fluid F, the seal member 22 is sucked and slides backward in the clearance 27. Then the seal member 22 is butted to the rear end stopper 26, thereby reaching a rear dead point (Ref. FIGS. 2 and 5A).

In this embodiment, the front end portion of the sliding member 20, or the front end face of the sleeve 21 is flush with or recessed from the front end of the main cylinder 12, when the sleeve 21 is at the dead point of the forward movable range.

Accordingly, the sleeve 21 is kept from sticking forward from the main cylinder 12, upon squeezing out the O-ring 50 thereby detaching the O-ring 50 from the front end of the suction tube 17. The sleeve 21 is, therefore, kept from contacting the hemorrhoid 100 or a peripheral diseased part.

The hemorrhoid ligation apparatus 10 includes a fixing member 44 that fixes a relative position of the sub cylinder 14 backwardly drawn and the main cylinder 12.

Actual shape or location of the fixing member 44 is not specifically limited. In this embodiment, a projection 45 formed on an outer circumferential surface of the main cylinder 12 and a mating portion 46 formed on the sub cylinder 14 are engaged with each other, to thereby relatively fix the main cylinder 12 and the sub cylinder 14.

The projection 45 or the mating portion 46 may be provided in a plurality of numbers along the sliding direction of the sub cylinder 14, so as to provide a plurality of engaging positions. In this embodiment, a plurality of mating portions 46 is aligned along the inner surface of a clip 47, formed so as to project laterally from the engaging portion 48 of the sub cylinder 14. Accordingly, in the case of changing the drawing distance of the sub cylinder 14 from the main cylinder 12 for optionally controlling the amount of the hemorrhoid 100 to be sucked, one of the mating portions 46 can be selected for engaging with the projection 45.

In the hemorrhoid ligation apparatus 10 according to this embodiment, the main cylinder 12 is made of a transparent material. Examples of the transparent material include glass, and transparent resin materials such as a polycarbonate resin, a polyvinyl chloride resin, an acrylic resin, or a polymer alloy thereof.

In the hemorrhoid ligation apparatus 10 according to this embodiment, the sub cylinder 14 and the plunger 16 are also made of a transparent material. Specifically, similar materials to those for the main cylinder 12 may be cited.

In this embodiment, the front end portion 60 constitutes an extended portion of the main cylinder 12 along the sliding direction of the sub cylinder 14. In other words, the hemorrhoid ligation apparatus 10 is of a linear type with the straight front end portion.

Hereunder, description will be given on a method of ligating the hemorrhoid 100 utilizing the hemorrhoid ligation apparatus 10 according to this embodiment.

This is a method of ligating the hemorrhoid 100 with the O-ring 50 attached to an outer circumferential surface of the front end portion of the main cylinder 12, including:

a first process including drawing the sub cylinder 14 airtightly and slidably provided inside the main cylinder 12 and a plunger 16 air-tightly and slidably provided inside the sub cylinder 14 together toward the rear end portion of the main cylinder 12, to thereby suck the hemorrhoid 100 into inside the front end portion of the main cylinder 12; and a second process including squeezing the plunger 16 toward the front end portion of the sub cylinder 14 to thereby pressurize the operating fluid F loaded inside the sub cylinder 14, so as to cause the pressurized operating fluid F to squeeze the O-ring 50 toward the front end of the main cylinder 12 thus detaching the O-ring 50 from the main cylinder 12, and ligating the hemorrhoid 100 with the detached O-ring 50.

As shown in FIG. 6, the hemorrhoid ligation apparatus 10 according to this embodiment is used in combination with an anoscope 110. The anoscope 110 generally includes a funnel portion 112 having a small-diameter tip portion, a scope spacer (not shown) set in a cavity of the funnel portion 112, and a handle 114 provided at a large-diameter rear end portion of the funnel portion 112. The funnel portion 112 includes a slit provided on an upper portion thereof, opposite to the handle 114.

The operator holds the handle 114 with one hand (not the dominant one), and inserts tip portion of the funnel portion 112 with the scope spacer set therein into the anus of the patient. Then upon visually locating the hemorrhoid 100 after removing the scope spacer, the operator sets the hemorrhoid ligation apparatus 10 on the funnel portion 112, and adjusts the orientation of the hemorrhoid ligation apparatus 10 utilizing the slit, so as to direct the front end portion 60 to the hemorrhoid 100.

The O-ring 50 is attached to an outer circumferential surface of the suction tube 17 from the front end thereof, in an initial state of the hemorrhoid ligation apparatus 10 as shown in FIGS. 2, 3A and 3B, i.e. with the plunger 16 drawn by a predetermined distance from the sub cylinder 14, so that the seal member 22 is butted to the rear end stopper 26. Once the O-ring 50 is attached, the sleeve 21 is pushed backward and butted to the seal member 22. Thus, the sliding member 20 including the sleeve 21 and the seal member 22 is set at the dead point of the backward movable range.

When attaching the O-ring 50, it is preferable to employ, for example, a conical expanding device 76 (Ref. FIGS. 9A to 9C, and 10A and 10B). Specific method of attaching the O-ring 50 with the expanding device 76 will be subsequently described.

The hemorrhoid ligation apparatus 10 in the foregoing initial state is combined as described above with the anoscope 110 shown in FIG. 6, and applied to the hemorrhoid 100 of the patient.

Then as the first operation (first process), the sub cylinder 14 and the plunger 16 are drawn backward with respect to the main cylinder 12 as shown in FIG. 4A, to thereby suck the hemorrhoid 100 into the suction tube 17. Under such state, upon engaging the projection 45 with the mating portion 46, the sub cylinder 14 is fixed to the main cylinder 12. The state where the hemorrhoid 100 is being sucked into the suction tube 17 is shown in FIG. 5A.

Then as the second operation (second process), the plunger 16 is squeezed forward into the sub cylinder 14, as shown in FIG. 4B. Accordingly, the operating fluid F pressurized inside the sub cylinder 14 squeezes the seal member 22 and the sleeve 21 toward the front end, thereby detaching the O-ring 50 from the suction tube 17.

The state where the hemorrhoid 100 is ligated by the O-ring 50 is shown in FIG. 5B.

The O-ring 50 shrinks in diameter because of its own elastic restoring force as indicated by an arrow in FIG. 5B, thus ligating the hemorrhoid 100 being sucked into the suction tube 17.

Advantageous effects of the hemorrhoid ligation apparatus 10 according to this embodiment will now be described.

In the first operation with the hemorrhoid ligation apparatus 10 according to this embodiment, the sub cylinder 14 is drawn backward with respect to the main cylinder 12, to thereby suck the hemorrhoid 100 into the front end portion of the main cylinder 12. Then in the second operation, the plunger 16 is squeezed forward with respect to the sub cylinder 14, to thereby squeeze out the O-ring 50 from the front end of the main cylinder 12. Thus, the plunger 16 which serves to detach the O-ring 50 moves relatively backward in the first operation, and relatively forward in the second operation, with respect to the main cylinder 12. In other words, the relative moving direction of the plunger 16 and the main cylinder 12 turns opposite upon entering the second operation from the first operation. In the first operation, therefore, there is no likelihood that the operator unduly causes the plunger 16 to move forward with respect to the main cylinder 12, in other words, such improper operation as accidentally detaching the O-ring before the suction of hemorrhoid 100 can be prevented.

In contrast, in the case of the ligation apparatus according to the foregoing patented documents 2 and 3, the plunger is drawn backward with the thumb pusher and the housing being relatively fixed to each other in the first operation, and the thumb pusher is squeezed with the housing and the plunger being relatively fixed to each other, in the second operation. Thus, the thumb pusher which serves to detach the O-ring moves relatively forward with respect to the plunger, both in the first operation and the second operation. In other words, the relative moving direction of the thumb pusher and the plunger remains the same, during the first operation and the second operation. Besides, the thumb pusher is provided at an outer position of the housing and the plunger. Such structure leads to the drawback that, if the operator accidentally engages his/her finger with the thumb pusher located at an outer position, instead of the housing in the first operation, the second operation is performed before the hemorrhoid is sucked, thus to readily detach the O-ring.

In the foregoing hemorrhoid ligation apparatus 10 according to this embodiment, the relative moving direction of the main cylinder 12 which is the outer structure and hence easy for the operator to touch, and the plunger 16 which serves to detach the O-ring 50, is set to be opposite in the first operation and the second operation. Such structure offers the advantage that the improper operation by the operator can be prevented.

Also, the hemorrhoid ligation apparatus 10 according to this embodiment further includes the piping 32 having an end communicating with the sub cylinder 14 so as to allow the operating fluid F to flow through the piping, the sliding member 20 slidably attached to an outer circumferential surface of the front end portion of the main cylinder 12, so as to seal the other end of the piping 32 and to squeeze the O-ring 50 toward the front end portion of the main cylinder 12 according to the pressing force applied by the pressurized operating fluid F, and the rear end stopper 26 that delimits the backward movable range of the sliding member 20.

Accordingly, upon drawing the plunger 16 backward with respect to the sub cylinder 14, the pressure to the operating fluid F inside the sub cylinder 14 is reduced, so that the sliding member 20 sealing the piping 32 is sucked to the dead point of the backward movable range. Then upon drawing the plunger 16 further backward from the sub cylinder 14, the sliding member 20 is inhibited from moving further by the rear end stopper 26, so that the operating fluid F expands inside the sub cylinder 14, which leads to further depressurization. Then the sub cylinder 14 is subjected to the atmospheric pressure applied through the front end portion of the main cylinder 12, and moves backward together with the plunger 16.

Thus, even though the operator draws the plunger 16 backward, not the sub cylinder 14, in the first operation, when he or she should actually draw the sub cylinder 14 with respect to the main cylinder 12, this does not lead to an improper operation of the hemorrhoid ligation apparatus 10. It is because the sub cylinder 14 follows up the movement of the plunger 16 thus moving backward, which is the desired direction, so that the first operation is performed, and also because drawing the plunger 16 backward does not cause the O-ring 50 to come off.

The hemorrhoid ligation apparatus 10 according to this embodiment allows, consequently, executing the first operation and the second operation thereby properly ligating the hemorrhoid 100, without imposing limitation to the retaining position and operating position of the operator.

Also, the hemorrhoid ligation apparatus 10 according to this embodiment further includes the front end stopper 24 that delimits the forward movable range of the sliding member 20. Accordingly, the sliding member 20 is forced to stop at a predetermined position after squeezing out the O-ring 50 from the front end, irrespective of the magnitude of the pressing force applied to the sliding member 20 by the operating fluid F.

In contrast, with the ligation apparatus according to the foregoing patented documents 2 and 3, in the second operation of squeezing the thumb pusher so as to detach the O-ring, the tip portion of the thumb pusher may stick out beyond the housing, if pressed with an excessive force. In case where the thumb pusher thus sticking out is butted to the hemorrhoid or a peripheral diseased part, the patient may suffer a pain.

With the hemorrhoid ligation apparatus 10 according to this embodiment, however, since the front end stopper 24 serves to detain the sliding member 20, there is little likelihood that the sliding member 20 contacts the hemorrhoid 100 or a peripheral diseased part.

Also, in the hemorrhoid ligation apparatus 10 according to this embodiment, the front end face of the sliding member 20 becomes flush with or recessed from the front end face of the main cylinder 12, upon reaching the dead point of the forward movable range. Accordingly, the sliding member 20 is kept from sticking out from the main cylinder 12 after squeezing out the O-ring 50, and is hence kept from contacting the hemorrhoid 100 or a peripheral diseased part.

Also, the hemorrhoid ligation apparatus 10 according to this embodiment further includes the fixing member 44 that fixes the relative position of the sub cylinder 14 drawn backward and the main cylinder 12.

Such structure prevents the sub cylinder 14 from moving forward together with the plunger 16, in the second operation of squeezing the plunger 16 forward. Accordingly, the hemorrhoid 100 once sucked is kept from being unduly discharged from the main cylinder 12, during the second operation.

In this embodiment, the main cylinder 12 is made of a transparent material. This allows the operator to visually recognize the hemorrhoid ligation apparatus 10 through the main cylinder 12, upon inserting the hemorrhoid ligation apparatus 10 into the patient's anus expanded by the anoscope 110 to thereby suck the hemorrhoid 100 into the main cylinder 12.

In the hemorrhoid ligation apparatus 10 according to this embodiment, the front end portion 60 constitutes an extended portion of the main cylinder 12 along the sliding direction of the sub cylinder 14, and the sub cylinder 14 and the plunger 16 are both made of a transparent material.

In other words, the hemorrhoid ligation apparatus 10 is of a linear type with the straight front end portion. Accordingly, the hemorrhoid 100 to be sucked into the main cylinder 12 and ligated, the sub cylinder 14, and the plunger 16 are linearly aligned. In this case also, the operator can visually recognize the hemorrhoid 100 through the sub cylinder 14 and the plunger 16.

In this embodiment, the plunger 16 is constituted of a hollow transparent resin material, to upgrade the visibility through the plunger 16.

Second Embodiment

Figure 7:
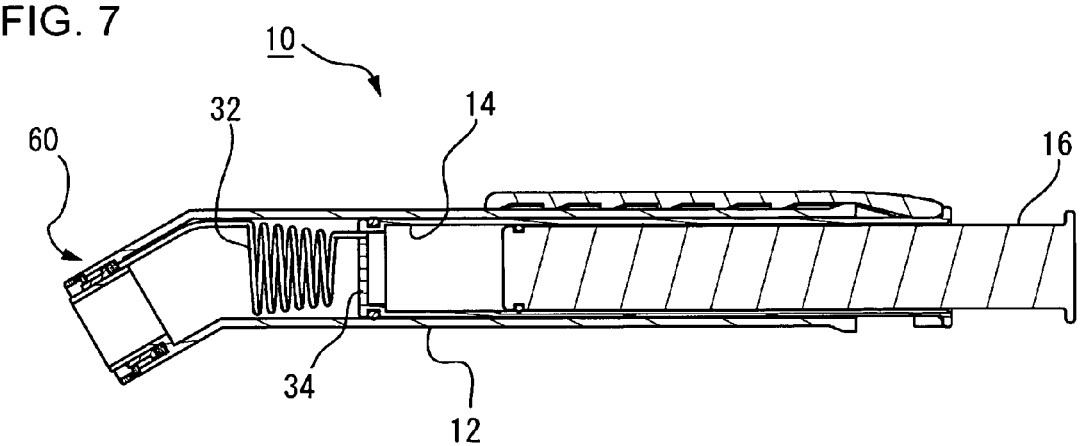
FIG. 7 is a vertical cross-sectional view showing a hemorrhoid ligation apparatus according to a second embodiment.
Figure 8:
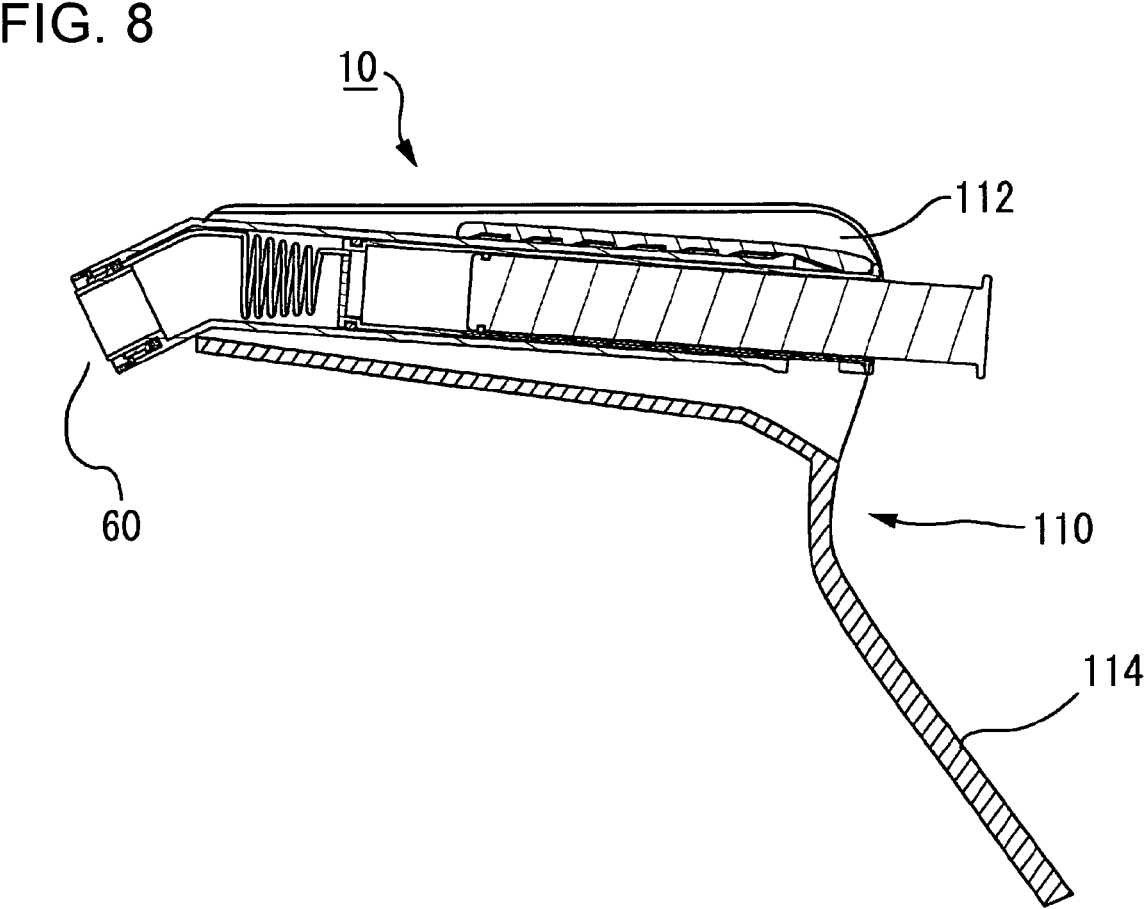
FIG. 8 shows the hemorrhoid ligation apparatus according to the second embodiment, mounted on an anoscope for actual use.

FIG. 7 is a vertical cross-sectional view showing a hemorrhoid ligation apparatus 10 according to a second embodiment. FIG. 8 shows the hemorrhoid ligation apparatus 10 according to this embodiment, mounted on the anoscope 110 for actual use.

The hemorrhoid ligation apparatus 10 according to this embodiment is different from that of the first embodiment in that the front end portion 60 of the main cylinder 12 extends in a direction that intersects with the sliding direction of the sub cylinder 14. In other words, the hemorrhoid ligation apparatus 10 according to this embodiment is of a bent type with the front end portion 60 of the main cylinder 12 formed in a bent shape.

Because of such structure, in the case where the insertion angle of the anoscope 110 into the patient's anus and the sliding direction of the sub cylinder 14 are aligned, the front end portion 60 of the main cylinder 12 (suction tube 17) is oriented to a different direction. Accordingly, when the operator attempts to visually recognize the hemorrhoid 100, the hemorrhoid 100 and the sub cylinder 14 or the plunger 16 are not linearly aligned. Therefore, this embodiment provides better visibility of the hemorrhoid 100. And as long as the main cylinder 12 is of a transparent material, the sub cylinder 14 or the plunger 16 does not have to be made of a transparent material.

In the case of the bent-type hemorrhoid ligation apparatus 10 also, since the piping 32 is helically wound and hence the apparent length can expand or shrink, the piping 32 can expand or shrink following up the sliding movement of the sub cylinder 14, remaining connected between the front end face 34 of the sub cylinder 14 and the front end portion 60 of the main cylinder 12.

It is to be noted that the present invention is not limited to the foregoing embodiments, but includes various modifications and improvements as long as the object of the present invention is achieved.

For example, in the first or the second embodiment, the sliding member 20, the front end stopper 24 and the rear end stopper 26 may be excluded, so as to squeeze out the O-ring 50 to the front end of the main cylinder 12 with the injection pressure of the pressurized operating fluid F. In this case, the height of the clearance 27, i.e. the distance between the inner surface of the cover tube 18 and the outer surface of the suction tube 17 may be made equal to the thickness of the O-ring 50, and the O-ring 50 may be set inside the clearance 27. Under such structure, upon injecting the pressurized operating fluid F into the clearance 27, the O-ring 50 can be emitted forward like a pop gun, to thereby ligate the hemorrhoid 100.

Also, the piping 32 may be a rigid through pipe extending backward from the fluid hole 28 and penetrating through the front end face 34 of the sub cylinder 14, instead of the helically wound and elastic structure as the foregoing embodiments. Such through pipe is inserted deeper into the sub cylinder 14 than the stroke of the sub cylinder 14 to be traveled in the first operation, so that the through pipe does not fall off from the fluid hole 36 of the sub cylinder 14, despite drawing the sub cylinder 14 backward with respect to the main cylinder 12 in the first operation. With such structure, the space defined by the inner surface of the main cylinder 12 including the suction tube 17 and the front end face 34 of the sub cylinder 14 is made air-tight except for the front opening of the suction tube 17, and hence the hemorrhoid 100 can be sucked into the suction tube 17 by manipulating the sub cylinder 14. In the second operation also, upon squeezing the plunger 16 into the sub cylinder 14, the pressurized operating fluid F is squeezed toward the clearance 27 from the sub cylinder 14 communicating via the through pipe, so as to cause the sliding member 20 to slide forward thus detaching the O-ring 50, as in the foregoing embodiments.

Inside the clearance 27, a ring-shaped spring may be provided between the front end stopper 24 and the sleeve 21. This applies a backward bias to the sleeve 21, and hence the sleeve 21 can only slide forward when the operating fluid F is subjected to a pressure greater than a predetermined level, in the second operation of detaching the O-ring 50. Accordingly, the operator can be prevented from committing the improper operation of unduly detaching the O-ring 50, even though he or she erroneously squeezes the plunger 16, when applying the hemorrhoid ligation apparatus 10 to the hemorrhoid 100, as well as in the first operation of sucking the hemorrhoid 100 into the main cylinder 12, and therefore the foregoing advantage of the present invention can be further enhanced.

[Method of Attaching the O-Ring and Ligation Kit]

Figure 9A:
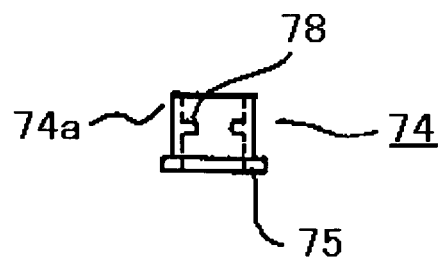
FIGS. 9A to 9C show a tubular body, a substrate and an expanding device respectively, included in an O-ring attaching device according to the embodiment.
Figure 9B:
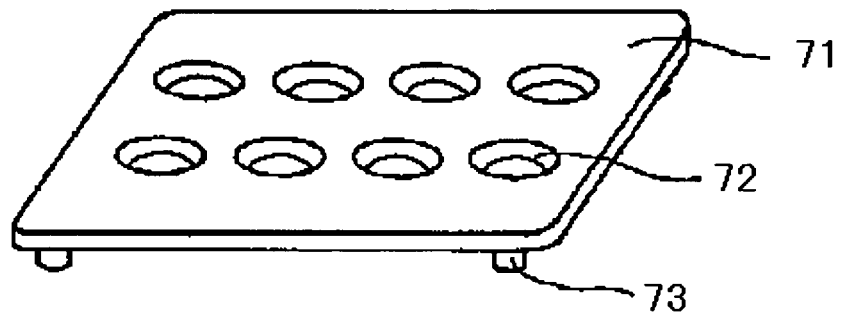
Figure 9C:
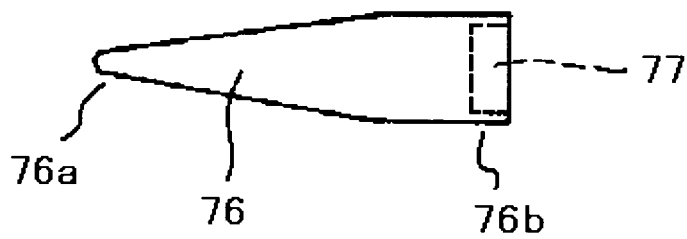

FIGS. 9A to 9C show constituents of an O-ring attaching device 70 according to the embodiment of the present invention. The O-ring attaching device 70 is a jig employed for attaching the O-ring 50 to the front end portion of the hemorrhoid ligation apparatus 10, and constitutes a ligation kit together with the hemorrhoid ligation apparatus 10 and the O-ring 50.

FIG. 9A shows a tubular body 74 having an inner diameter larger than the outer diameter of the front end portion of the main cylinder 12 (suction tube 17). FIG. 9B shows a substrate 71 including at least a hole 72 through which the tubular body 74 is to be slidably inserted. FIG. 9C shows a state where a base portion 76b of the expanding device 76 is placed on an upper end portion 74a of tubular body 74 exposed from the hole 72. The expanding device 76 is of a tapered shape, such that the tip portion 76a is smaller in diameter than the base portion 76b.

The substrate 71 includes a projection 73 on each of the four corners on the lower face thereof (lower side in FIG. 9B).

On the lower end of the tubular body 74, a flange 75 is provided which is larger in diameter than the hole 72. Upon inserting the of the tubular body 74 through the hole 72 from the lower side, the upper end portion 74a is exposed from the hole 72.

At a middle height of the tubular body 74, an inner rib 78 is provided so as to inwardly protrude. The inner rib 78 has a smaller diameter than the outer diameter of the front end portion of the main cylinder 12 (suction tube 17).

The base portion 76b of the expanding device 76 includes a recessed portion 77, in which the upper end portion 74a of the tubular body 74 can be fitted and attached.

The tubular body 74 may include, instead of the inner rib 78 formed so as to protrude from the inner wall, a stepped portion at a middle height such that the lower portion has a smaller inner diameter, in other words a thicker wall.

Figure 10A:
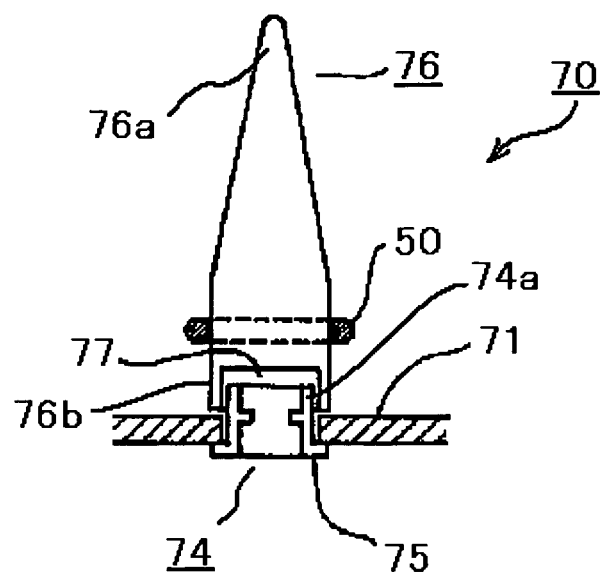
FIGS. 10A and 10B show a process of mounting the O-ring on the O-ring attaching device according to the embodiment.
Figure 10B:
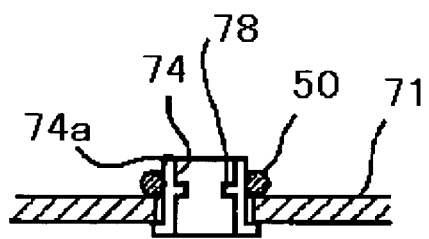

FIGS. 10A and 10B show a process of mounting the O-ring 50 on the O-ring attaching device 70 according to this embodiment. FIG. 10A shows a state where the recessed portion 77 of the expanding device 76 is attached to the upper end portion 74a of the tubular body 74 inserted through the substrate 71 from below, and then the O-ring 50 is caused to slide downward while expanding, from the small-diameter tip portion 76a toward the base portion 76b of the expanding device 76.

FIG. 10B shows a state where the expanding device 76 has been removed, after transferring the O-ring 50 from the base portion 76b or the expanding device 76 to the upper end portion 74a of the tubular body 74.

The inner diameter of the hole 72 provided on the substrate 71 is larger than the outer diameter of the upper end portion 74a of the tubular body 74, but smaller than the outer diameter of the O-ring 50 attached to the upper end portion 74a.

Accordingly, the tubular body 74 with the O-ring 50 attached to the upper end portion 74a is kept from falling off because of the self weight thereof, from the substrate 71.

In the case of the substrate 71 including a plurality of holes 72 as in this embodiment, the tubular bodies 74 may be inserted through the respective holes 72 from below, to thereby attach the O-ring 50 to the upper end portion 74a of each tubular body 74, utilizing the expanding device 76.

On the other hand, the outer diameter of the front end portion of the suction tube 17 (Ref. FIG. 2) is smaller than the inner diameter of the tubular body 74, but larger than the inner diameter of the inner rib 78. Accordingly, upon pressing the tubular body 74 downward applying the front end face of the suction tube 17 of the hemorrhoid ligation apparatus 10 to the upper end portion 74a under the state of FIG. 10B, the tubular body 74 falls off from the substrate 71, and the O-ring 50 is transferred from the upper end portion 74a to the suction tube 17.

Here, since the inner diameter of the cover tube 18 (Ref. FIG. 2) is larger than the outer diameter of the O-ring 50 attached to the tubular body 74, the cover tube 18 can be kept from interfering in the step of attaching the O-ring 50 to the suction tube 17.

Also, it is preferable to make the projections 73 higher than the height of the tubular body 74, so as to allow the tubular body 74 to fall off from the substrate 71 upon being pressed downward by the suction tube 17.

The O-ring 50 transferred to the outer circumferential surface of the front end portion of the suction tube 17 serves to ligate the hemorrhoid 100, upon being detached in the second operation as described above.

Then the operator can press down another tubular body 74 inserted through the substrate 71 with the suction tube 17 from the upper end portion 74a, to thereby transfer the O-ring 50 attached to the relevant tubular body 74, to the suction tube 17.

Thus, the ligation kit according to this embodiment allows setting a plurality of O-rings 50 in advance to on the substrate 71, thereby facilitating the operator to easily attach the O-ring 50 by one touch to the front end portion of the suction tube 17, under the state where the operator retains the anoscope 110 by a hand and the hemorrhoid ligation apparatus 10 by the other hand.

It is apparent that the present invention is not limited to the above embodiment, and may be modified and changed without departing from the scope and spirit of the invention.

The invention claimed is:

1. A hemorrhoid ligation apparatus, comprising:
   a main cylinder to which an O-ring for ligating a hemorrhoid is to be attached, on an outer circumferential surface of a front end portion;
   a sub cylinder air-tightly and slidably provided inside said main cylinder, so as to suck said hemorrhoid into said front end portion of said main cylinder upon being drawn toward a rear end portion of said main cylinder;
   an operating fluid loaded inside said sub cylinder; and
   a plunger air-tightly and slidably provided inside said sub cylinder, so as to pressurize said operating fluid upon being squeezed toward a front end portion of said sub cylinder, to thereby squeeze said O-ring toward said front end portion of said main cylinder with said operating fluid being pressurized, thus detaching said O-ring from said main cylinder.

2. The hemorrhoid ligation apparatus according to claim 1, further comprising:
   a piping having an end communicating with said sub cylinder so as to allow said operating fluid to flow through said piping;
   a sliding member slidably attached to an outer circumferential surface of said front end portion of said main cylinder, so as to seal the other end of said piping and to squeeze said O-ring toward said front end portion of said main cylinder according to a pressing force applied by said operating fluid being pressurized;
   a front end stopper that delimits a forward movable range of said sliding member; and
   a rear end stopper that delimits a backward movable range of said sliding member.

3. The hemorrhoid ligation apparatus according to claim 2, wherein a front end of said sliding member becomes flush with or recessed from said front end portion of said main cylinder, upon reaching a dead point of said forward movable range.

4. The hemorrhoid ligation apparatus according to claim 1, further comprising a fixing member that fixes a relative position of said sub cylinder drawn backward and said main cylinder.

5. The hemorrhoid ligation apparatus according to claim 1, wherein said main cylinder is constituted essentially of a transparent material.

6. The hemorrhoid ligation apparatus according to claim 5, wherein
   said front end portion of said main cylinder constitutes an extended portion of said main cylinder,
   said front end portion of the main cylinder is oriented along a sliding direction of said sub cylinder, and
   said sub cylinder and said plunger are both constituted essentially of a transparent material.

7. The hemorrhoid ligation apparatus according to claim 5, wherein
   said front end portion of said main cylinder constitutes an extended portion of said main cylinder,
   said extended portion of said main cylinder is formed in a bent shape, and
   said front end portion of the main cylinder is oriented to a different direction from a sliding direction of the sub cylinder.

8. A ligation kit, comprising:

said hemorrhoid ligation apparatus according to claim 1;

one or more O-rings for attachment to said outer circumferential surface of said front end portion of said main cylinder; and an O-ring attaching device including:
- (a) a tubular body having a larger inner diameter than an outer diameter of said front end portion of said main cylinder,
- (b) a substrate including at least one hole through which an upper end portion of said tubular body is to be slidably inserted, and
- (c) a tapered-shape expanding device having a tip portion smaller in diameter than a base portion thereof, to be removably fitted on the upper end portion of said tubular body exposed through said hole, via said base portion, wherein an inner diameter of said hole is larger than an outer diameter of the upper end portion of the tubular body, and is smaller than an outer diameter of an O-ring attached to the upper portion of the tubular body.

9. A method of ligating a hemorrhoid with an O-ring attached to an outer circumferential surface of a front end portion of a main cylinder, comprising:

a first process including drawing a sub cylinder air-tightly and slidably provided inside said main cylinder and a plunger air-tightly and slidably provided inside said sub cylinder together toward a rear end portion of said main cylinder, to thereby suck said hemorrhoid into inside said front end portion of said main cylinder; and a second process including squeezing said plunger toward a front end portion of said sub cylinder to thereby pressurize an operating fluid loaded inside said sub cylinder, so as to cause said operating fluid to be pressurized to squeeze said O-ring toward said front end portion of said main cylinder thus detaching said O-ring from said main cylinder, and ligating said hemorrhoid with said O-ring thus detached.

* * * * *